United States Patent [19]
Sheridan et al.

[11] 3,973,569
[45] Aug. 10, 1976

[54] TRACHEOSTOMY TUBE DEVICE WITH NECK SIZE ADJUSTMENT MEANS

[75] Inventors: David S. Sheridan, Argyle; Isaac S. Jackson, Greenwich, both of N.Y.

[73] Assignee: National Catheter Corporation, Argyle, N.Y.

[22] Filed: Aug. 6, 1975

[21] Appl. No.: 602,433

[52] U.S. Cl............................ 128/351; 128/DIG. 26
[51] Int. Cl.² ......................................... A61M 25/00
[58] Field of Search ........... 128/351, 348, 283, 295, 128/DIG. 26

[56] References Cited
UNITED STATES PATENTS

| | | | |
|---|---|---|---|
| 2,786,469 | 3/1957 | Cohen | 128/351 |
| 3,137,299 | 6/1964 | Tabor | 128/351 |
| 3,225,767 | 12/1965 | Smith | 128/351 |

*Primary Examiner*—Stephen C. Pellegrino
*Attorney, Agent, or Firm*—Kemon, Palmer & Estabrook

[57] ABSTRACT

Tracheostomy tubes are provided with means that permits them to be held firmly in proper position upon a person on whom the device is installed. Such means comprises a fixed flange member, a slideable flange member and a plurality of slideable and separately removeable ring members positioned between the fixed and slideable flange members.

5 Claims, 5 Drawing Figures

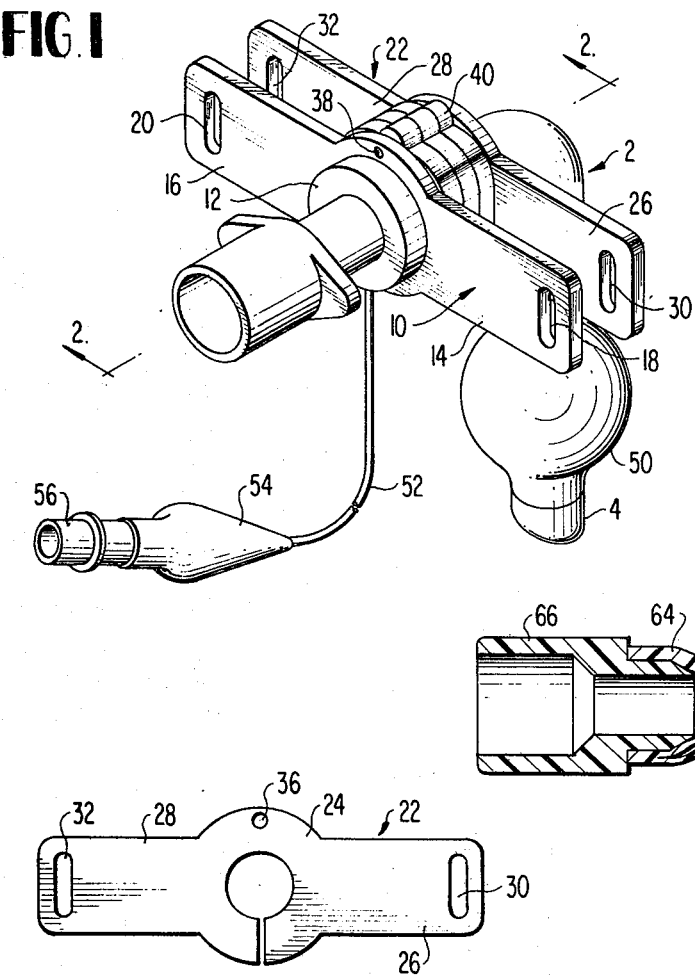
FIG. 1
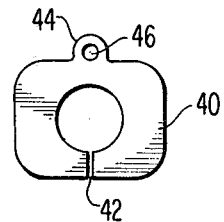
FIG. 4
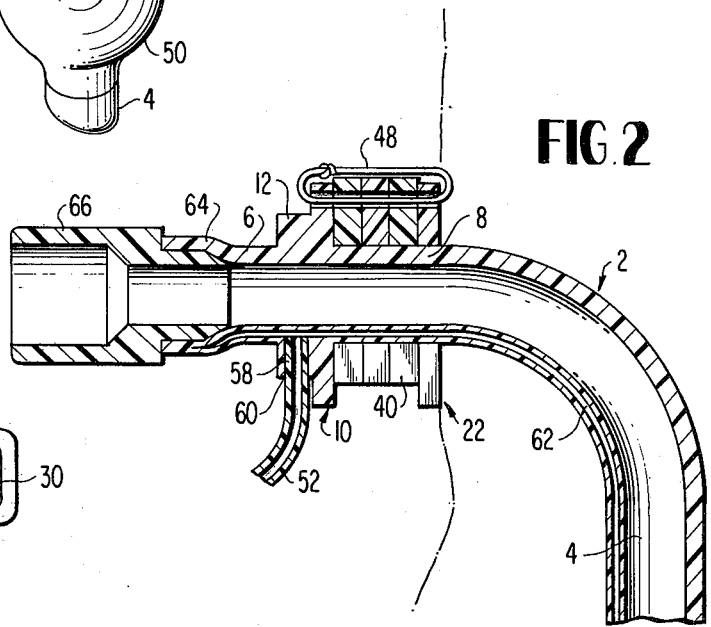
FIG. 2
FIG. 5
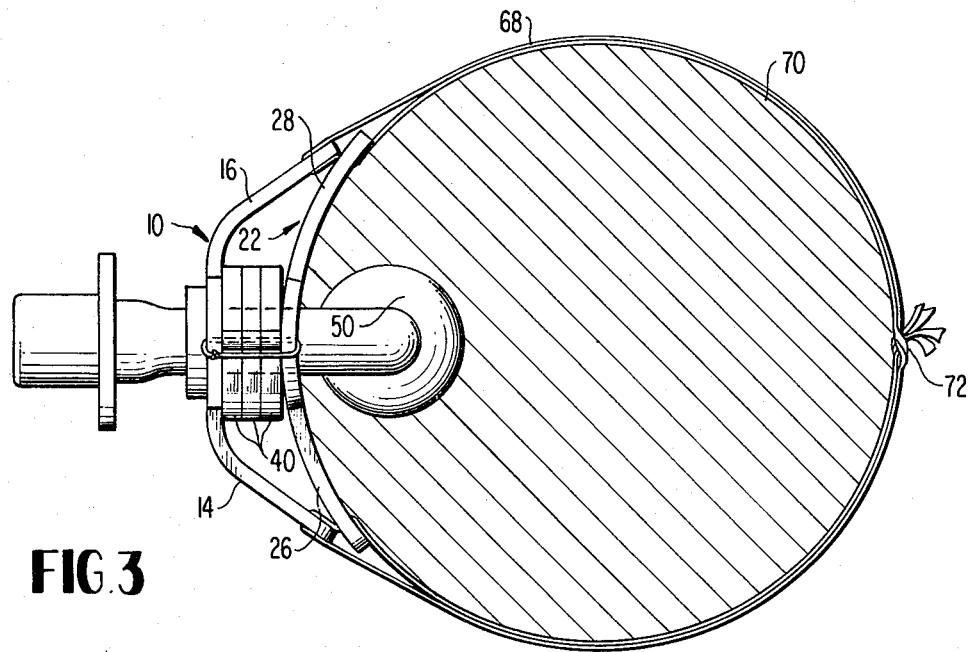
FIG. 3

TRACHEOSTOMY TUBE DEVICE WITH NECK SIZE ADJUSTMENT MEANS

BACKGROUND OF THE INVENTION

1. Field of the Invention

This invention relates to tracheostomy tube devices. More particularly, it concerns such devices that are improved by adjustable neck flange means which permits the device to be held firmly in proper position upon a person whom the device has been installed regardless of the neck size of such person.

2. Description of the Prior Art

Tracheostomy tubes generally have neck flanges fixed thereon to provide means for holding the tube in proper position after it has been inserted into a patient using a tie tape which is fastened around the neck of the patient. Due to the many variations in human anatomy, (fat, thin, short, tall, etc.), the industry has had to provide many variations in curvature, length, etc. There have been attempts by others to make an adjustable flange. One is nothing more than a flange which slides on the tube. This is hazardous because it does just that; the tube is not securely held in position. Another method provides a threaded, collet type encirclement which closes radially around the tube when a "nut" is tightened. This compresses the tube, making a section of reduced diameter. As the plastic takes a "set", the flange can move.

Another form of neck size adjustment in tracheostomy tubes involves a tube provided with spaced-apart annular beads that cooperate with a slideable ring. (see U.S. Pat. No. 3,137,299).

A still further form of neck adjustment, although of limited scope, uses a plurality of slots in the neck flange to provide length adjustment for a neck encircling band (see U.S. Pat. No. 1,835,757).

Other size adjustment systems are known, but they are cumbersome or difficult to adjust. A need exists for adjustable neck flange units for tracheostomy tubes that are inexpensive to manufacture, give a full range of adjustability, are easy to use and do not adversely effect the tube device or its use.

OBJECTS

A principle object of the invention is to provide new and improved forms of tracheostomy tubes.

A further object is the provision of tracheostomy tubes capable of being held firmly in proper position upon a person on whom the tube has been installed regardless of the neck structure of such person.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished according to the invention by providing tracheostomy tube devices with an improvement which enables them to adjust to variations in neck anatomy of the users of the devices. Such improvement comprises a first flange member fixed upon the tubular section of the exocorporeal portion of the tracheostomy tube device, a second flange member slideably held on the tubular section and a plurality of slideable and separately removable ring members positioned between the fixed and slideable flange members. The flange members have end slots to receive tie tape and the flanges and ring members have aligned holes to provide connection means.

BRIEF DESCRIPTION OF THE DRAWINGS

For a more complete understanding of the invention, reference is made to the accompanying drawing in which:

FIG. 1 is an isometric view of an improved tracheostomy tube device of the invention.

FIG. 2 is a fragmentary sectional view taken on the line 2—2 of FIG. 1.

FIG. 3 is a diagramatic plan view of the device of FIG. 1 fixed upon the neck of a patient.

FIG. 4 is a plan view of a split ring member of the new tracheostomy tube device.

FIG. 5 is a plan view of the slideable flange member of the new device.

DESCRIPTION OF THE PREFERRED EMBODIMENT

Referring in detail to the drawing, the tracheostomy tube device 2 comprises an endotracheal portion 4 and an exocorporeal portion 6 defined in part by a tubular section 8 formed of non-fibrous plastic material.

A first flange member 10 formed of flexible, non-fibrous plastic material is formed with a central ring portion 12 and a pair of opposed wing portions 14 and 16. Slots 18 and 20 are provided in the ends of wing portions 14 and 16 respectively. The flange member 10 is fixed on the tubular section 8 such as by solvent welding or use of adhesive.

A second flange member 22 is formed of flexible, non-fibrous plastic material to have a central ring portion 24 and a pair of opposed wing portions 26 and 28 having slots 30 and 32 in the ends thereof. The central ring portion 24 has a split 34 in the bottom and a small hole 36 opposite to the split. A similar hole 38 is provided in the top of the central ring portion 12 of flange member 10. The second flange member 22 slideably encircles the tubular section 8.

A plurality of ring members 40 formed of flexible, non-fibrous plastic material slideably encircle the tubular section 8. The members 40 have a split 42 therein and a small lug 44 through which a hole 46 extends. The holes 36, 38 and 46 are at substantially the same radial position relative to the central axis of the tubular section 8 so the holes can all be aligned as seen in FIG. 2 and a cord passed through them to tie together the flange members 10 and 22 with the ring members 40.

The device 2 has a balloon cuff 50 on the endotracheal portion 4. An inflation tube 52 provided with pilot balloon 54 and check valve 56 is attached to the exocoporeal portion 6 by having its distal end 58 cemented into the hole 60 in the forward part of the central ring portion 12. A secondary lumen 62 communicates the inflation tube 52 with the balloon cuff 50 to enable the balloon cuff to be inflated when the device 2 is positioned in a patient.

The proximal end 64 of the device 2 has fitted therein a molded plastic tubing connector 66 by which the device 2 may be connected to a gas supply in accordance with standard procedure as required by the patient.

The tubing connector is preferably molded from rigid plastic, e.g., nylon, polyethylene, polypropylene or the like. The remaining portions of the device 2 are made of flexible plastic, e.g., plasticized polyvinyl chloride. All of the components can be made of the same soft durometer flexible plastic. Hence, there is no need for metal or hard plastic parts that can cause discomfort to the patient.

In practice the device 2 will be enclosed in wrapper or package and sterilized such as by exposure to ethylene oxide vapors. When the use of the device is required, the surgeon will remove the sterile device from the package and then "fit" it to the patient. The endotracheal portion with the balloon cuff deflated is inserted through an incision in the throat of the patient (see FIG. 2) usually between the thyroid cartilage and the cricoid. The portion 4 of the device extends downwardly within the patient's trachea. The problem in the "fitting" of the device to the patient is to have the endotracheal portion 4 centered within the trachea. To do this, the device must accomodate for the depth or thickness of the patient's throat forward of the trachea, i.e., it is not the circumference of the throat that is critical. The device 2 is structured so that the surgeon can make the fit by removing parts rather than unscrewing or by disconnecting a part from one point and reconnecting at another point. The size adjustment is made by removing one or more of the split ring members 40 from the tubular section 8. In special cases requiring the greatest depth of insertion, all the ring members 40 as well as the second flange member 22 can be removed leaving only the fixed flange member 10.

When the required number of ring members 40 are in position, the assembly can be fixed together by the tie thread or cord 48. This tying is a safety feature to prevent accidental dislodgement of separable parts.

The device 2 is then firmly held in the proper position on the patient by passing a tie tape 68 through the slots 18 and 30 at one side, passing the tape around the patient's neck (diagramatically shown as 70 in FIG. 3), through the slots 20 and 32 at the other side and then tied with a knot 72. When the device is in place in this manner, lateral movement of the exocoporeal portion 6 is mitigated by the trussed structure presented by the overlapped wings 14, 26 and 16, 28 as seen in FIG. 3.

The balloon cuff can be expanded as required by introduction of air through the valve 56. However, the neck size adjustment means of the invention can be used also on tracheostomy tube devices that do not include a balloon cuff.

If after several days of use of one of the devices, the surgeon decides to replace it with a new one, he only need set up the same combination of flanges and split ring members on the new device to get the same proper fit on the patient, i.e., no new measurement is required.

The embodiments of the invention in which an exclusive property or privilege is claimed are defined as follows:

1. In a tracheostomy tube device having an endotracheal portion and an integral exocorporeal portion defined in part by a tubular section formed of non-fibrous plastic material, the improvement which permits the device to be held firmly in proper position upon a person into whom the endotracheal portion has been inserted regardless of the neck size of such person, the improvement which comprises:
   A. a first flange member formed of flexible, non-fibrous plastic material comprising a central ring portion and a pair of opposed wing portions extending therefrom,
   B. the tubular section of the device being fixedly encircled by said central ring portion,
   C. a second flange member formed of flexible, non-fibrous plastic material comprising a central ring portion and a pair of opposed wing portions extending therefrom,
   D. the tubular section of the device being slideably encircled by the central ring portion of said second flange member,
   E. a split in the central ring portion of the second flange member whereby it may be removed from around said tubular section,
   F. a plurality of split ring members formed of flexible, non-fibrous plastic material encircling said tubular section positioned between said first and second flange members, and
   G. a slot in the outer end of each wing portion of said first and second flange members through which tie tape may be passed to be tied around the neck of a person on which said tube device is installed.

2. The tracheostomy tube device of claim 1 wherein:
   a. the central ring portion of said second flange has a hole therethrough diametrically opposed to said split therein,
   b. a hole through the central ring portion of said first flange member at the top thereof,
   c. a hole through each of said split ring members,
   d. all of said holes of items a, b and c being at substantially the same radial position relative to the central axis of said tubular section whereby the holes may be aligned and a cord passed through them to tie together the first and second flange member and the split ring members.

3. The tracheostomy tube device of claim 1 having:
   a. balloon cuff on the endotracheal portion,
   b. a inflation tube attached to the exocoporeal portion and
   c. a secondary lumen communicating said inflation tube with said balloon cuff.

4. The tracheostomy tube device of claim 1 wherein the proximal end thereof is fitted with a molded plastic tubing connector.

5. The tracheostomy tube device of claim 1 wherein all the stated parts thereof are formed of plasticized polyvinyl chloride resin.

* * * * *